United States Patent [19]

Sheldon

[11] Patent Number: 4,676,773
[45] Date of Patent: Jun. 30, 1987

[54] COMPACT TAMPON TUBE APPLICATOR

[75] Inventor: Donald A. Sheldon, Appleton, Wis.

[73] Assignee: Kimberly-Clark Corporation, Neenah, Wis.

[21] Appl. No.: 800,005

[22] Filed: Nov. 20, 1985

Related U.S. Application Data

[63] Continuation-in-part of Ser. No. 640,199, Aug. 13, 1984, abandoned.

[51] Int. Cl.$^4$ ............................................. A61F 5/44
[52] U.S. Cl. ...................................... 604/16; 604/11; 604/14; 604/904
[58] Field of Search ................................... 604/12–16, 604/53, 904

[56] References Cited

U.S. PATENT DOCUMENTS

| | | |
|---|---|---|
| 2,829,646 | 4/1958 | Kurkjian . |
| 3,090,385 | 5/1963 | Brecht . |
| 3,115,876 | 12/1963 | Nalle, Jr. . |
| 3,749,094 | 7/1973 | Daincan .............................. 604/904 |
| 3,753,437 | 8/1973 | Hood et al. ............................ 604/16 |
| 3,831,605 | 8/1974 | Fournier . |
| 3,998,225 | 12/1976 | Hytonen . |
| 4,048,998 | 9/1977 | Nigro . |
| 4,198,978 | 4/1980 | Nigro .................................... 604/14 |
| 4,276,881 | 7/1981 | Lilaonilkul .......................... 604/16 |
| 4,286,595 | 9/1981 | Ring . |
| 4,329,991 | 5/1982 | Sakurai . |
| 4,411,647 | 10/1983 | Sakurai et al. ....................... 604/16 |
| 4,479,791 | 10/1984 | Sprague ................................ 604/14 |

FOREIGN PATENT DOCUMENTS

| | | |
|---|---|---|
| 1049894 | 11/1966 | United Kingdom . |
| 2033754 | 5/1980 | United Kingdom . |
| 2081586 | 2/1982 | United Kingdom . |

*Primary Examiner*—C. Fred Rosenbaum
*Assistant Examiner*—John D. Ferros
*Attorney, Agent, or Firm*—Paul A. Leipold; Donald L. Traut; Jeremiah J. Duggan

[57] ABSTRACT

A compact tube applicator is provided in which a nesting telescoping inner tube has slits on its leading edge to receive the tampon pledget and a ring positioned around the trailing end, the trailing end being narrower in diameter than the leading end when the inner tube is pulled backward, the tampon is expelled through the leading ends of the two tubes by the inwardly compressive forces provided by the ring.

11 Claims, 11 Drawing Figures

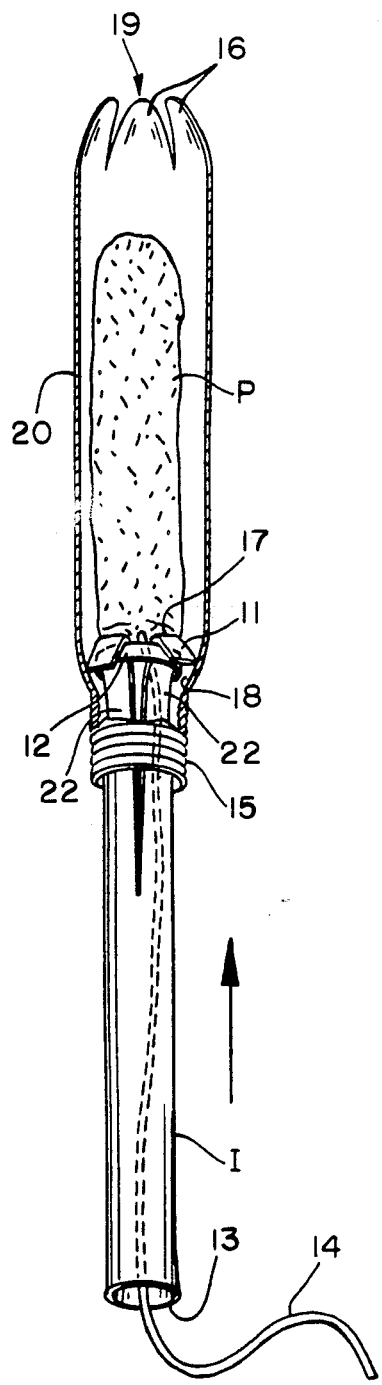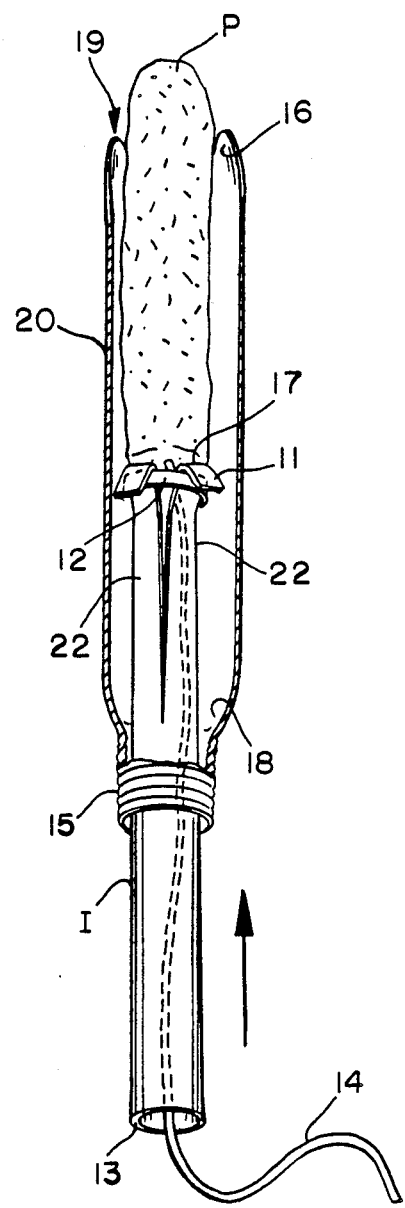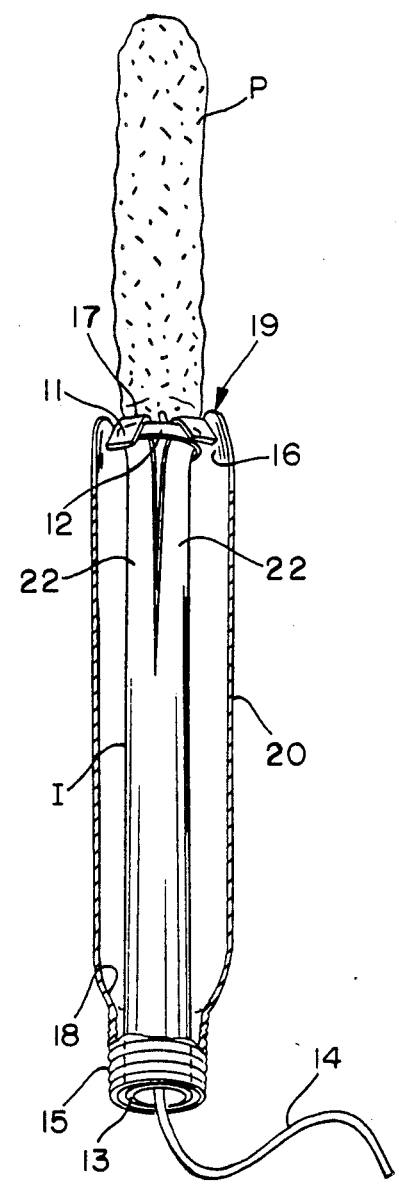
FIG. 9
FIG. 10
FIG. 11

4,676,773

COMPACT TAMPON TUBE APPLICATOR

This is a continuation-in-part of Ser. No. 640,199 filed Aug. 13, 1984 now abandoned.

FIELD OF THE INVENTION

This invention relates to a tampon applicator and particularly to a compact applicator having telescoping inner and outer tubes.

BACKGROUND OF THE INVENTION

Tampons are inserted by the wearer either by direct insertion via the fingers of the wearer or else by means of a tampon applicator. Tampons applicators have proven to be the insertion means of choice by a substantial proportion of tampon users in the United States. There are several considerations involved in the construction of applicators. These applicators are conventionally made either of a cardboard or a molded thermoplastic material. While applicators made of thermoplastic material are anesthetically desirable because they tend to cover the leading edge of the tampon pledget prior to insertion and resist absorption of bodily fluids, the relative cost of these applicators is substantially higher than the cost of comparable cardboard applicators. Since the applicators do not directly affect the products performance, but do have a direct affect on the overall cost of the tampon unit, it is desirable to provide inexpensive tampon applicators which means minimal use of material and simplicity of design particularly in the case of applicators made of thermoplastic material. Complex molding not only adds to the cost but produces undesirable flash which may injure the user.

Aesthetically, tampons are used in part for discreteness and portability and therefore the applicators should be as small as possible. The most often used tampon applicators are made in the form of telescoping tubes with inner tubes designed to be withdrawn from the rearward or gripping edge of the outer tube and then pushed back against the tampon pledget to expel the pledget through the insertion end or edge of the outer tube.

Because of the desirability for discreteness, several tampon tubes have been suggested which provide for positioning the tampon pledget within at least a portion of the inner tube. The leading edge of the inner tube is then compressed as the inner tube is withdrawn through the insertion end of the outer tube. The compression of the diameter of the leading end of the inner tube constricts the end to a diameter less than the pledget diameter and provides and edge for pushing the pledget out through the leading or insertion end of the outer tube. U.S. Pat. No, 4,276,881 describes such an applicator. U.S. Pat. No. 3,090,385 describes a tampon applicator with several extended fingers instead of an inner tube. These fingers are compressed by a ring fashioned as part of an inner surface of the outer tube.

U.S. Pat. No. 4,286,595 discloses another type of radially compressible inner tube with alternating slots and grooves. In each of the applicators described above, either the inner or outer tube requires some complicated structure either to provide a detent or a restraint for the reciprocal motion of the inner tube.

SUMMARY OF THE INVENTION

According to this invention a tampon applicator of compact length has telescoping inner and outer tubes of a simple construction with slits extending from the leading end i.e. tampon pledget receiving end of the inner tube which allow the slit ends to expand to receive the tampon and provide edges which are folded backward to form flanges. The narrow i.e. trailing end of the inner tube is encircled by a separate ring element which has an outer diameter greater than a necked-in finger gripping diameter of the outer tube. When inner tube is withdrawn to provide a pushing surface for the tampon pledget it is compressed by its contact with the inner circumferences of this annular member. The flanges are formed by bending the outer split ends of the tampon receiving inner tube and a sliding ring provides a detent which prevents the removal of the inner tube during its withdrawal from the tampon pledget.

BRIEF DESCRIPTION OF THE DRAWINGS

The invention may be more readily understood by reference to the drawings in which:

FIGS. 6 through 11 are illustrations in partial section of the steps in operation of the tampon applicator of the invention.

MODES OF THE INVENTION

The invention has several advantages over previous tampon applicators. It is compact in size; further, it is low in cost, not requiring particularly complicated formation methods. Further it is effective in achieving positive ejection of the tampon pledget from the applicator as the tampon is prevented by the ring from returning into the split inner tube. Another advantage is that the operation of the applicator is simple and consistent with previous tampon applicators in operation by the user.

Figure 1:
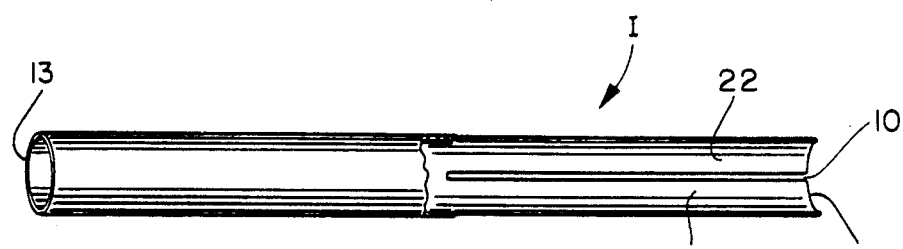
FIGS. 1, 2, and 3 are representative side views of stages of assembly of the inner tube.

This can be seen in FIG. 1 an inner tampon tube I is formed with a slit 10 at the leading or tampon insertion edge 17 while the slit 10 extends downward towards the opposite end 13 and terminates substantially before reaching the end. At least two such slits are necessary to accomplish the insertion and compression associated with this invention and preferably four or five slits are utilized.

Figure 2:
Figure 3:
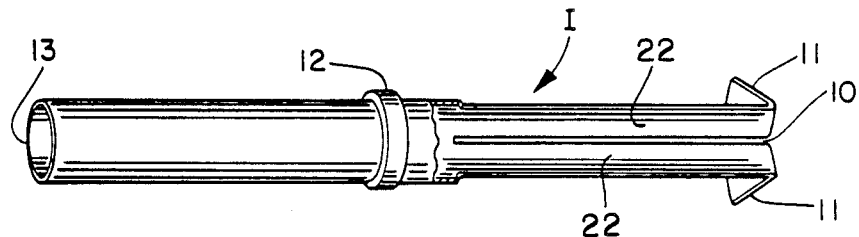

After the slits have been cut flanges 11 are folded backward as seen in FIG. 2. Flanges 11 are designed to be engaged by ring 12 as can be seen in FIG. 3 but the flange is extended radially outwardly beyond the inner diameter of the annular member 12.

Figure 4:
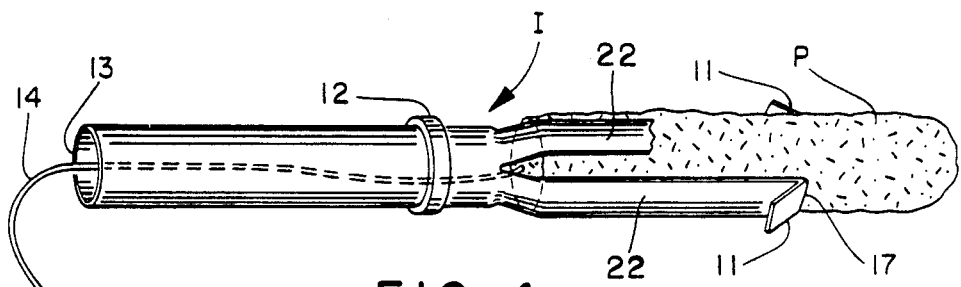
FIG. 4 is a cross-sectional view of an assembled inner tube with the tampon pledget inserted.
Figure 5:
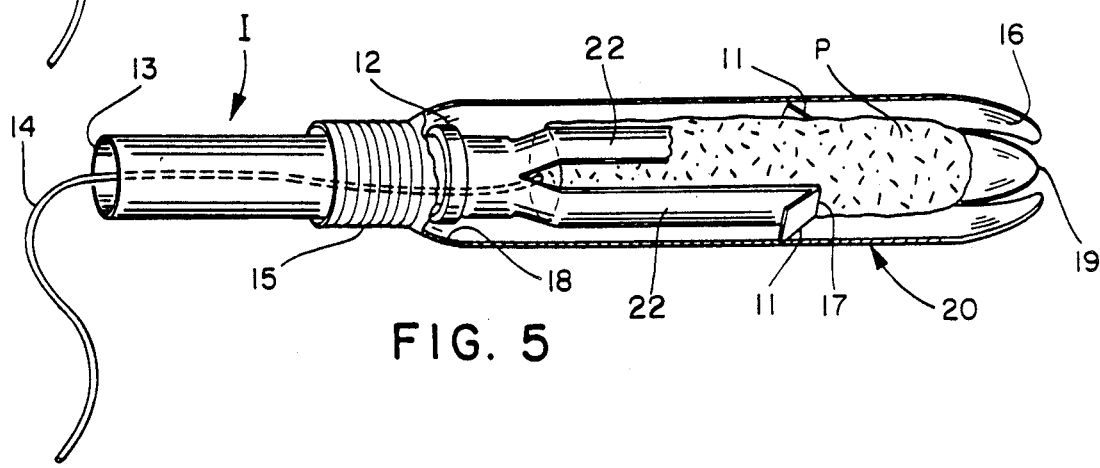
FIG. 5 is a cross-sectional view of the inner and outer tube after assembly with tampon pledget.

As can be seen in FIG. 4 a tampon pledget P having a withdrawal string 14 is inserted by spreading the tampon insertion end 17 of the inner tube I radially to form fingers 22. The pledget P extends beyond the folded flange 11 but as can be seen to FIG. 5, still encompassed within the petals 16 of the insertion end 19 of outer tube 20. In this particularly preferred embodiment, as is well known in the art, the petals 19 are compressed to form a bullet-shaped leading edge of the outer tube for ease of insertion by the wearer. The outer tube 20 has shoulder 18 which tapers into a radially reduced finger gripping portion 15. The inner diameter of the finger portion 15, can be seen in FIG. 5, is smaller than the outer diameter of the annular member 12. As the inner tube is withdrawn toward the finger gripping portion and is compressed by the action of the ring on the leading end 17, the ring stays within the outer tube and is not expelled from the finger gripping portion.

Figure 6:
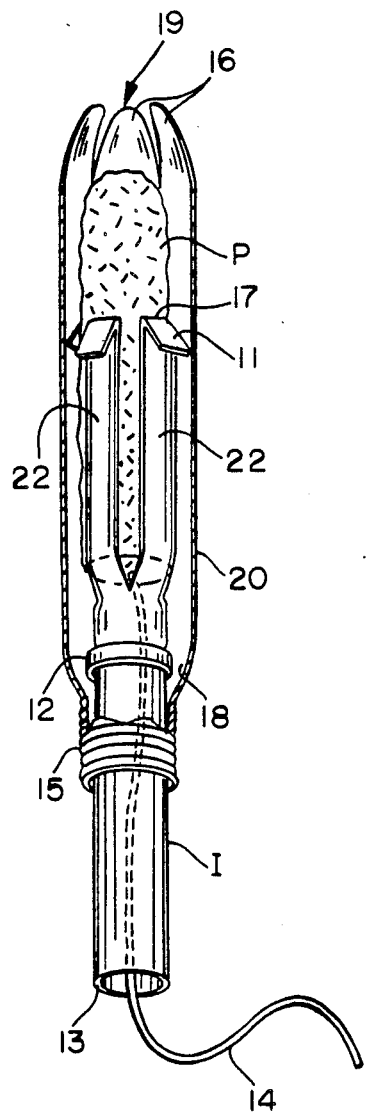

FIGS. 6 through 11 illustrate the application of the tampon applicator of the invention. As illustrated in FIG. 6, the tampon is in the condition as it is wrapped and stored prior to use. The insertion end 19 has petals 16 closed while the fingers 22 of the inner tube I have been forced open by the pledget P. Ring 12 is loosely around the inner tube 13 resting on shoulder 18.

Figure 7:
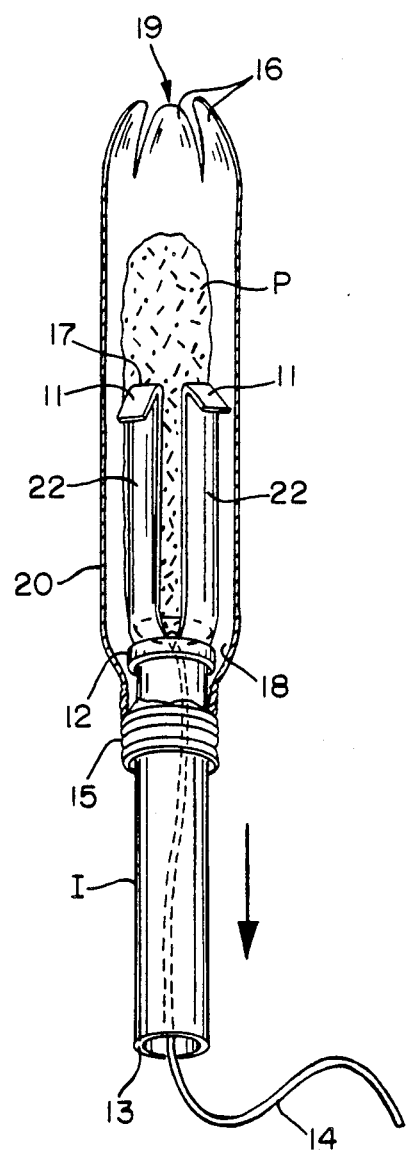

In FIG. 7 the inner tube I has been withdrawn to a point where ring 12 engages the portion of fingers 22 that have been extended radially around the pledget P. Ring 12 has a greater diameter than the inner diameter of finger gripping portion 15 and rests against the shoulders 18.

Figure 8:
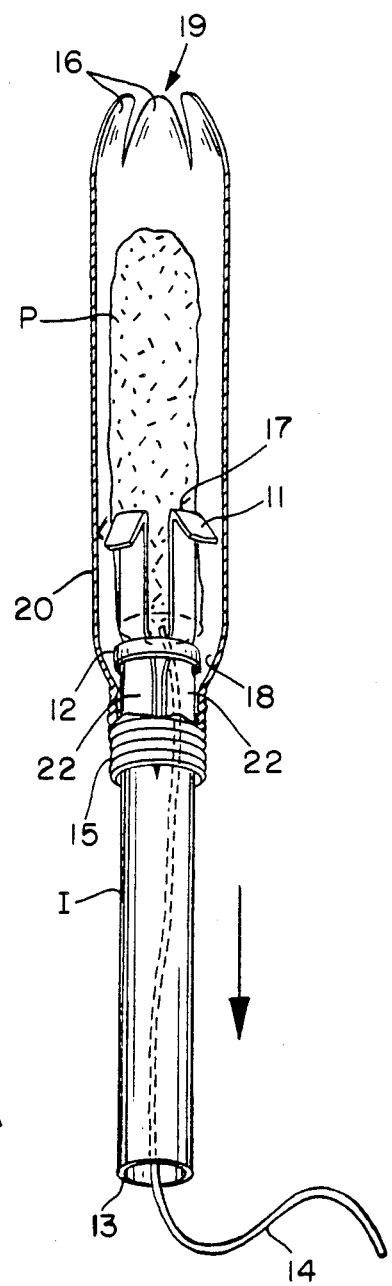

FIG. 8 illustrates the inner tube I withdrawn part way and the ring 12 has collapsed fingers 22 together such that the pledget is forced out from the area below where ring 12 is engaged around fingers 22.

FIG. 9 illustrates where the pledget P has been completely forced from between fingers 22 and loosely rests within outer tube 20. Ring 12 is beneath flanges 11 where the fingers 22 have been turned over at 17. It is noted that the flanges 11 may be of such length that they generally ride on the inner wall of outer tube 20 during the withdrawal and reinsertion of inner tube I.

FIG. 10 illustrates partial reinsertion of inner tube I to force pledget P out of the insertion end 19 by forcing open petals 16. The ring 12 is engaged with and stays in place by the pressure of fingers 22 to keep the pledget P from being reinserted into the inner tube I.

FIG. 11 illustrates the pledget P completely ejected from outer tube 20 with the petals 16 completely open and the inner tube I generally completely inserted into the outer tube 20. At this stage, the applicator device is removed from the vagina of the user and may be discarded. The string 14 will slip through the inner tube I as the applicator outer tube 20 is removed.

The tampon insertion device of the instant invention may be formed of any suitable materials. Typical of suitable materials are plastics such as polyethylene or polypropylene. The polyethylenes would perferably be low density (LDPE) or linear low density (LLDPE) types. Further the inner and outer tubes could be different materials. Other suitable materials include cardboard.

It is also known and within the art to apply known lubricants to the tampon applicator and/or to the pledget to decrease friction of insertion of the tampon.

As can be seen, each of the elements of the tube assembly are simple to mold, require not complex assembly and provide a compact tampon applicator which can be made either from thermoplastic material in readily moldable shapes or from cardboard.

I claim:

1. A compact tampon applicator comprising an outer tampon tube with an insertion end and a gripping end and an inner tube and an annular member having:
   (a) a tampon pledget-surrounding leading end of said inner tube, positioned circumferentially inward from said insertion end of said outer tube while the pledget is stored therein, said leading end having a plurality of slits extending essentially parallelly downward along the tube length and a plurality of flanges extending radially outward from said leading end
   (b) a trailing end of said inner tube positioned radially inward from the gripping end of said outer tube when the tampon is stored in said leading end, said trailing end having substantially reduced diameter when compared to said leading end; and said annular member circumferentially surrounding said trailing end, said annular member having an inner diameter greater than the outer diameter of said trailing end but smaller than the diameter of said leading end, said annular member having an outer diameter greater than the inner diameter of said gripping end of said outer tube wherein when said inner tube is withdrawn through said griping end said annular member compresses said leading end expelling said tampon from said leading end and narrowing said leading end so that the leading end may be pressed against said tampon to expel it from said insertion end of said tampon tube.

2. The tampon applicator of claim 1 wherein said annular member is engaged with said flanges upon withdrawal of said inner tube.

3. The tampon applicator of claim 1 wherein said annular member rests against a shoulder formed in the outer tube in the area where it narrows to the diameter of said gripping end.

4. The tampon applicator of claim 1 wherein said inner and outer tubes are formed of plastic.

5. A compact tampon applicator comprising an inner tube, a sliding member engaging said inner tube and an outer tube wherein said inner tube comprises a tubular member slit at the insertion end into a multiplicity of fingers having a flange on the ends of at least one of said fingers and wherein said outer tube is of larger diameter at the insertion end than at the griping end and wherein said inner tube passes through said gripping end but said sliding member cannot pass through said gripping end.

6. The tampon applicator of claim 5 wherein said pledget is placed between the split ends of said inner tube.

7. The tampon applicator of claim 5 wherein said sliding member has an inner diameter such that it cannot slide past said flanges.

8. The tampon applicator of claim 5 wherein said outer tube is provided with petals that are opened when expelling a pledget from said outer tube.

9. The tampon of claim 5 wherein said flanges are formed by bending the ends of said fingers outward.

10. The tampon applicator of claim 5 wherein said a shoulder is formed in the area of said outer tube where the tube is narrowed to the gripping diameter.

11. The tampon applicator of claim 10 wherein said shoulder stops said sliding member and forces it into contact with said engaging contact with said flange when said inner tube is withdrawn.

* * * * *